US011357437B2

(12) United States Patent
Katz et al.

(10) Patent No.: US 11,357,437 B2
(45) Date of Patent: Jun. 14, 2022

(54) AUTOMATIC IDENTIFICATION OF ABNORMAL LAT DIFFERENCES

(71) Applicant: Biosense Webster (Israel) Ltd., Yokneam (IL)

(72) Inventors: Natan Sharon Katz, Kiryat Bialik (IL); Benjamin Cohen, Haifa (IL); Lior Zar, Poria Illit (IL); Vincent Alexandre Roger, Caluire-et-Cuire (FR)

(73) Assignee: Biosense Webster (Israel) Ltd., Yokneam (IL)

( * ) Notice: Subject to any disclaimer, the term of this patent is extended or adjusted under 35 U.S.C. 154(b) by 226 days.

(21) Appl. No.: 16/512,561

(22) Filed: Jul. 16, 2019

(65) Prior Publication Data

US 2020/0060568 A1 Feb. 27, 2020

Related U.S. Application Data

(60) Provisional application No. 62/723,218, filed on Aug. 27, 2018.

(51) Int. Cl.
*A61B 5/339* (2021.01)
*A61B 5/287* (2021.01)
(Continued)

(52) U.S. Cl.
CPC .............. *A61B 5/339* (2021.01); *A61B 5/066* (2013.01); *A61B 5/287* (2021.01); *A61B 5/318* (2021.01);
(Continued)

(58) Field of Classification Search
CPC ......... A61B 5/287; A61B 5/346; A61B 5/318; A61B 5/339; A61B 5/062; A61B 5/066; A61B 5/743
See application file for complete search history.

(56) References Cited

U.S. PATENT DOCUMENTS 6,301,496 B1 * 10/2001 Reisfeld .................. G06T 17/20 600/407
2009/0262992 A1 * 10/2009 Markowitz ............ A61B 5/742 382/128

(Continued)

OTHER PUBLICATIONS

European Search Report for corresponding EPA No. 19193440.5 dated Nov. 26, 2019.
Blanchard S M et al: "Activation mappingof ventricular fibrillation", Engineering in Medicine and Biology Society, Proceedings of the 15th Annual International Conference, of the IEEE Oct. 28—Oct. 28, 1993 (Oct. 28, 1993), pp. 861-862.

(Continued)

*Primary Examiner* — Jennifer Pitrak McDonald
*Assistant Examiner* — Pamela M. Bays
(74) *Attorney, Agent, or Firm* — Dergosits & Noah LLP; Todd A. Noah

(57) ABSTRACT

Apparatus, consisting of a catheter that is configured to be inserted into a chamber of a heart and that has one or more electrodes configured to contact myocardial tissue at multiple locations in the chamber. The one or more electrodes receive electrical signals responsive to a conduction wave traveling through the tissue. The apparatus includes a display and a processor that is configured to receive the electrical signals from the catheter and to render to the display, responsively to the electrical signals, a map of the chamber including an indication of local times of occurrence of the conduction wave at the multiple locations. The processor is also configured to calculate, responsively to the local times of occurrence, a velocity of the conduction wave between the locations and to mark on the map one or more areas of the chamber in which the velocity is below a preset threshold.

16 Claims, 5 Drawing Sheets

(51) Int. Cl.
*A61B 5/318* (2021.01)
*A61B 5/346* (2021.01)
*A61B 5/06* (2006.01)
*A61B 5/00* (2006.01)

(52) U.S. Cl.
CPC .............. *A61B 5/346* (2021.01); *A61B 5/743* (2013.01); *A61B 5/062* (2013.01)

(56) References Cited

U.S. PATENT DOCUMENTS

| | | | | |
|---|---|---|---|---|
| 2011/0251505 | A1* | 10/2011 | Narayan .............. | A61B 5/7278 600/515 |
| 2016/0106376 | A1* | 4/2016 | Li .......................... | A61B 5/743 600/373 |
| 2017/0172508 | A1* | 6/2017 | Huitz ................... | A61B 5/6852 |
| 2017/0311833 | A1 | 11/2017 | Afonso et al. | |

OTHER PUBLICATIONS

Raiman Michael et al: "Automated isochronal late activation mapping to identify deceleration zones: Rationale and methodology of a practical electroanatomic mapping approach for ventricular tachycardia ablation", Computers in Biology and Medicine, vol. 102, Jul. 18, 2018 (Jul. 18, 2018), pp. 336-340.
C.D. Cantwell et al.: "Techniques for automated local activation time annotation and conduction velocity estimation in cardiac mapping", Computers in Biology and Medicine., vol. 65, Apr. 25, 2015 (Apr. 25, 2015), pp. 229-242.
Kei Yano et al., "Electorphysiology of a gap created on the canine atrium", Journal of Interventional Cardiac Electrophysiology, vol. 17, No. 1, pp. 1-9, Jan. 26, 2007.
Bierhuizen M F A et al., "In calcineurin-induced cardiac hypertrophy expression of Na"v1.5, Cx40 and Cx43 is reduced by different mechanisms", Journal of Molecular and Cellular Cardiology, vol. 45, No. 3, pp. 373-384, Sep. 1, 2008.

* cited by examiner

AUTOMATIC IDENTIFICATION OF ABNORMAL LAT DIFFERENCES

CROSS-REFERENCE TO RELATED APPLICATIONS

This application claims the benefit of U.S. Provisional Patent Application 62/723,218 filed Aug. 27, 2018, which is incorporated herein by reference.

FIELD OF THE INVENTION

This invention relates generally to electrophysiological potentials, and specifically to identification of tissue having abnormal electrophysiological potentials.

BACKGROUND OF THE INVENTION

A standard method for cardiac investigation comprises producing maps of local activation times (LATs) of chambers of a beating heart. A "normal" heart, operating in sinus rhythm, produces well-defined LAT maps for the different chambers. A deviation from these maps allows a physician inspecting a map to identify possible problematic regions of the chambers. However, such identification may not be immediately obvious from the LAT map itself.

SUMMARY OF THE INVENTION

An embodiment of the present invention provides apparatus, including a catheter that is configured to be inserted into a chamber of a heart and that has one or more electrodes configured to contact myocardial tissue at multiple locations in the chamber and to receive electrical signals responsive to a conduction wave traveling through the tissue.

The apparatus also has a display, and a processor that is configured to receive the electrical signals from the catheter and to render to the display, responsively to the electrical signals, a map of the chamber including an indication of local times of occurrence of the conduction wave at the multiple locations. The processor also calculates, responsively to the local times of occurrence, a velocity of the conduction wave between the locations and marks on the map one or more areas of the chamber in which the velocity is below a preset threshold.

In a disclosed exemplary embodiment, the processor is configured to calculate interpolated local times of occurrence at respective positions between the multiple locations, and to mark on the map at the respective positions an indication of the interpolated local times of occurrence. Typically, the processor is configured to not mark on the map the indication of the interpolated local times of occurrence at the one or more areas.

In a further disclosed exemplary embodiment the processor is configured to divide the chamber into contiguous surfaces, each surface surrounding a respective one of the multiple locations, and the one or more areas are located at a border between two contiguous surfaces.

The processor may be configured to divide the chamber into the contiguous surfaces by forming a surface of the chamber as a set of voxels, and, for each given location of the multiple locations, iteratively and simultaneously adding an immediately neighboring voxel to a previous voxel, the previous voxel initially comprising a local originating voxel corresponding to the given location, so as to form a given contiguous surface.

The processor may also be configured to calculate the velocity of the conduction wave at a region on the border by finding a sum of the distances of the region to the respective locations of the two contiguous surfaces and dividing the sum by a time difference between the local times of occurrence at the respective locations.

In a yet further disclosed exemplary embodiment the electrical signals include electrocardiograph (ECG) signals, and the local times of occurrence correspond to local activation times (LATs) derived from the ECG signals. Typically, the processor is configured to incorporate into the map colors from a color scale having respective colors in a one-to-one correspondence with values of the LATs. The processor may be configured to color the one or more areas in a different color from colors of the color scale.

In an alternative embodiment the preset threshold is between 0.01 mm/ms and 1 mm/ms.

In a further alternative exemplary embodiment, the preset threshold is 0.1 mm/ms.

In a yet further alternative exemplary embodiment the catheter includes a position sensor configured to provide signals indicative of the multiple locations to the processor. Typically, the position sensor includes one or more coils which provide the signals in response to magnetic fields traversing the coils.

Another exemplary embodiment of the present invention provides a method, including:

inserting a catheter into a chamber of a heart, the catheter having one or more electrodes configured to contact myocardial tissue at multiple locations in the chamber and to receive electrical signals responsive to a conduction wave traveling through the tissue;

providing a display;

receiving the electrical signals from the catheter;

rendering to the display, responsively to the electrical signals, a map of the chamber including an indication of local times of occurrence of the conduction wave at the multiple locations;

calculating, responsively to the local times of occurrence, a velocity of the conduction wave between the locations; and marking on the map one or more areas of the chamber in which the velocity is below a preset threshold.

BRIEF DESCRIPTION OF THE DRAWINGS

The present disclosure will be more fully understood from the following detailed description of the embodiments thereof, taken together with the drawings, in which.

DETAILED DESCRIPTION OF EMBODIMENTS

Overview

Typically, in producing a local activation time (LAT) map of a chamber of the heart, a number of points on a surface of the chamber are sampled, and the LAT value for each of these points is calculated from the sampled data. The LAT values of points on the surface, intermediate the sampled points, are typically found by interpolation from the sampled points. The LAT values are typically incorporated into a 3D map of the chamber as different colors and the colored map, comprising sampled and interpolated LAT values, may then be presented to a physician for analysis.

However, the colored map by itself does not necessarily provide an indication of abnormal regions of the chamber, especially since in the case of abnormal regions the interpolation described above may give erroneous results and thus hide any unusual LAT values. For example, inspection of the colored map may give no indication whatsoever of a reduced velocity of a conduction wave travelling through the chamber, and such reduced velocity is indicative of an abnormal region.

Embodiments of the present invention provide a method, using further analysis of the sampled data, to indicate abnormal regions by estimating velocities of the conduction wave. The indication is provided on a "regular" LAT colored map, so that there is no need for production or viewing of a different map illustrating the conduction wave velocities.

Initially, a probe is inserted into the chamber being investigated, and the probe is used to acquire location data signals that are analyzed to give three-dimensional (3D) locations of the chamber surface. One or more electrodes on the probe, or on another probe, are also used to acquire timing data signals, typically electrocardiograph (ECG) signals, at selected locations on the surface. The ECG signals may be analyzed to calculate LAT values at the selected locations, and a map of the 3D chamber locations, with the LAT values incorporated into the map as colors, may be generated.

In addition to generating the map, the selected locations and their respective LAT values are analyzed to calculate velocities of the conduction wave at regions of the surface between the selected locations. When the velocity for a part of one of the regions is below a preset threshold, a visual indication is placed on the map at the part of the region.

DETAILED DESCRIPTION

Figure 1:
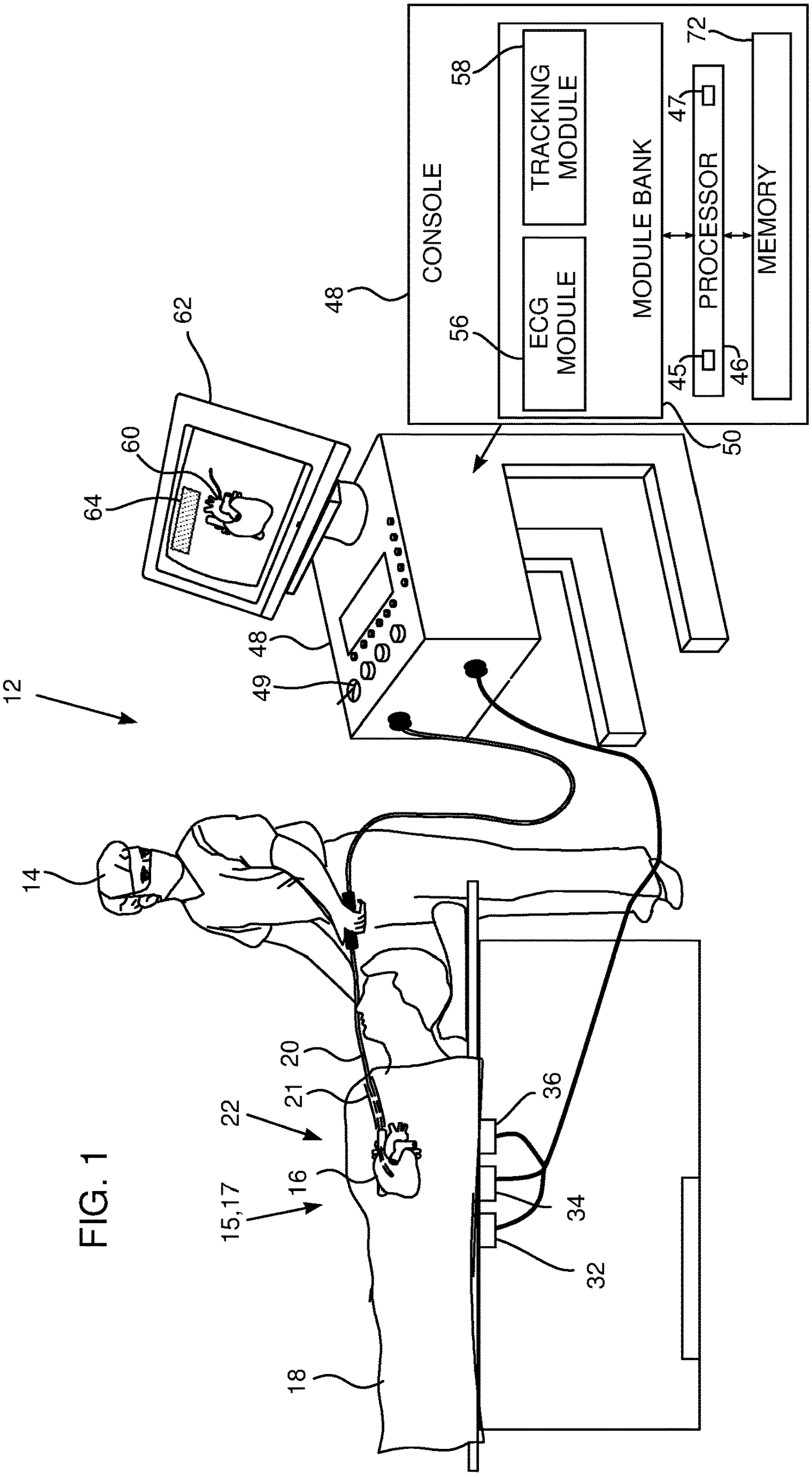
FIG. 1 is a schematic illustration of an invasive medical procedure using an apparatus, according to an embodiment of the present invention.
Figure 2:
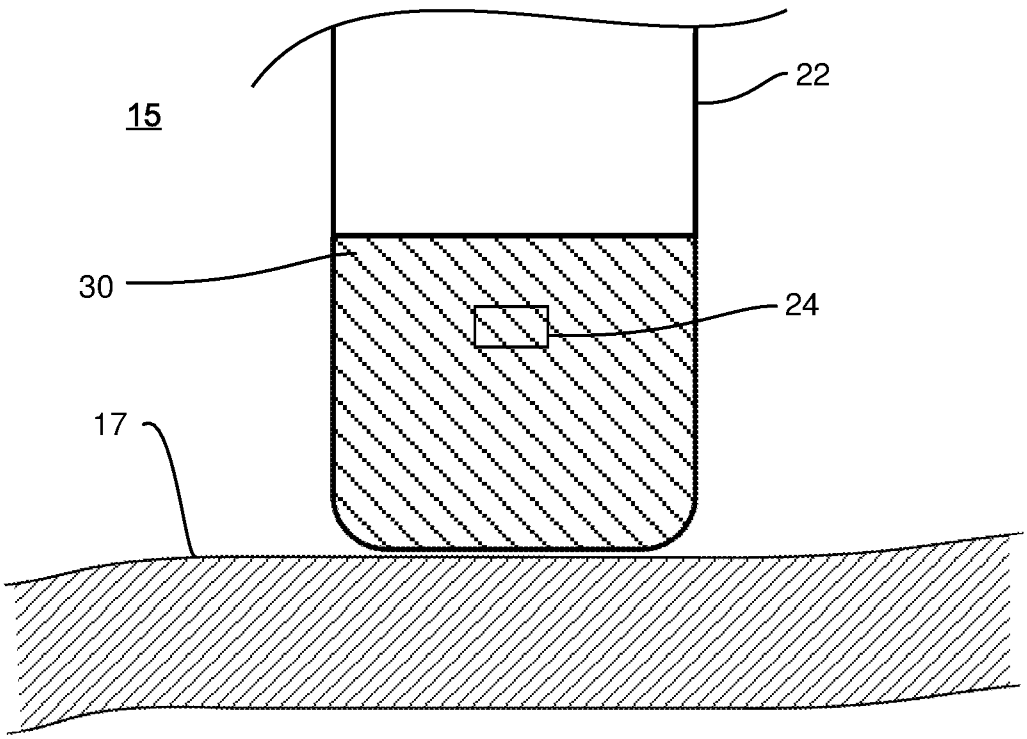
FIG. 2 is a schematic illustration of a distal end of a probe used in the apparatus, according to an embodiment of the present invention.

FIG. 1 is a schematic illustration of an invasive medical procedure using apparatus 12, and FIG. 2 is a schematic illustration of a distal end 22 of a catheter 20 used in the apparatus, according to an exemplary embodiment of the present invention. Catheter 20 is also referred to herein as probe 20. The procedure is performed by a medical professional 14, and in the description hereinbelow the procedure is assumed to comprise an electropotential (EP) investigation of a three-dimensional (3D) surface 17 of a chamber 15 of a heart 16 of a human patient 18.

In order to perform the investigation, medical professional 14 inserts probe 20 into a sheath 21 that has been pre-positioned in a lumen of the patient. Sheath 21 is positioned so that distal end 22 of the probe enters the heart of the patient. Distal end 22 comprises a position sensor 24 that enables the location and orientation of the distal end to be tracked. Distal end 22 also comprises one or more electrodes 30 which are used to acquire electropotentials from surface 17, as noted below. For clarity and simplicity, the following description assumes there is only one electrode 30.

Apparatus 12 is controlled by a system processor 46, which is located in an operating console 48 of the apparatus. Console 48 comprises controls 49 which are used by the medical professional 14 to communicate with the processor 46. The software for processor 46 may be downloaded to the processor 46 in electronic form, over a network, for example. Alternatively, or additionally, the software may be provided on non-transitory tangible media, such as optical, magnetic, or electronic storage media.

Electropotential (3D) data derived from EP signals acquired by electrode 30 is presented on a three-dimensional (3D) representation 60 of the heart of patient 18 that is formed on a display 62. The EP signals are generated in response to a conduction wave travelling through myocardial tissue of the heart.

In exemplary embodiments of the present invention, the 3D representation is presented using a color scale 64, where different colors are assigned respective different values, on a one-to-one basis, of a parameter derived from the EP data. The parameter used herein is a local activation time (LAT) of a region of surface 17, the LAT corresponding to a local time of occurrence of the conduction wave. In one exemplary embodiment the LAT varies from a low value of approximately −150 ms to a high value of approximately ms, as measured relative to a fiduciary reference signal, typically derived from a probe positioned in a coronary sinus of heart 16. In this case color scale 64 is preset as red for the low LAT value, violet for the high LAT value, and preset colors such as shades of orange, yellow, green, blue for intermediate LAT values.

System processor 46 comprises real-time noise reduction circuitry 45, typically configured as a field programmable gate array (FPGA), followed by an analog-to-digital (A/D) signal conversion integrated circuit 47. The processor 46 can pass the signal from A/D circuit 47 to another processor and/or can be programmed to perform at least one algorithm disclosed herein, the algorithm comprising steps described hereinbelow and being stored in a memory 72 in communication with processor 46. The processor uses circuitry 45 and circuit 47, as well as features of modules which are described in more detail below, in order to perform the algorithm.

In order to operate apparatus 12, the algorithm of processor 46 communicates with a module bank 50, which has a number of modules used by the processor to operate the apparatus. Thus, bank 50 comprises an electrocardiograph (ECG) module 56 which acquires and analyzes signals from electrode 30, and a tracking module 58 which receives and analyzes signals from position sensor 24, and which uses the signal analysis to generate a location and an orientation of distal end 22. In some exemplary embodiments sensor 24 comprises one or more coils which provide the sensor signals in response to magnetic fields traversing the coils. In these embodiments, in addition to receiving and analyzing signals from sensor 24, tracking module 58 also controls radiators 32, 34, and 36 which radiate the magnetic fields traversing sensor 24. The radiators 32, 34 and 36 are positioned in proximity to heart 16 and are configured to radiate alternating magnetic fields into a region in proximity to the heart. The Carto® system produced by Biosense Webster, of 33 Technology Drive, Irvine, Calif. 92618 USA, uses such a magnetic tracking system.

Figure 3:
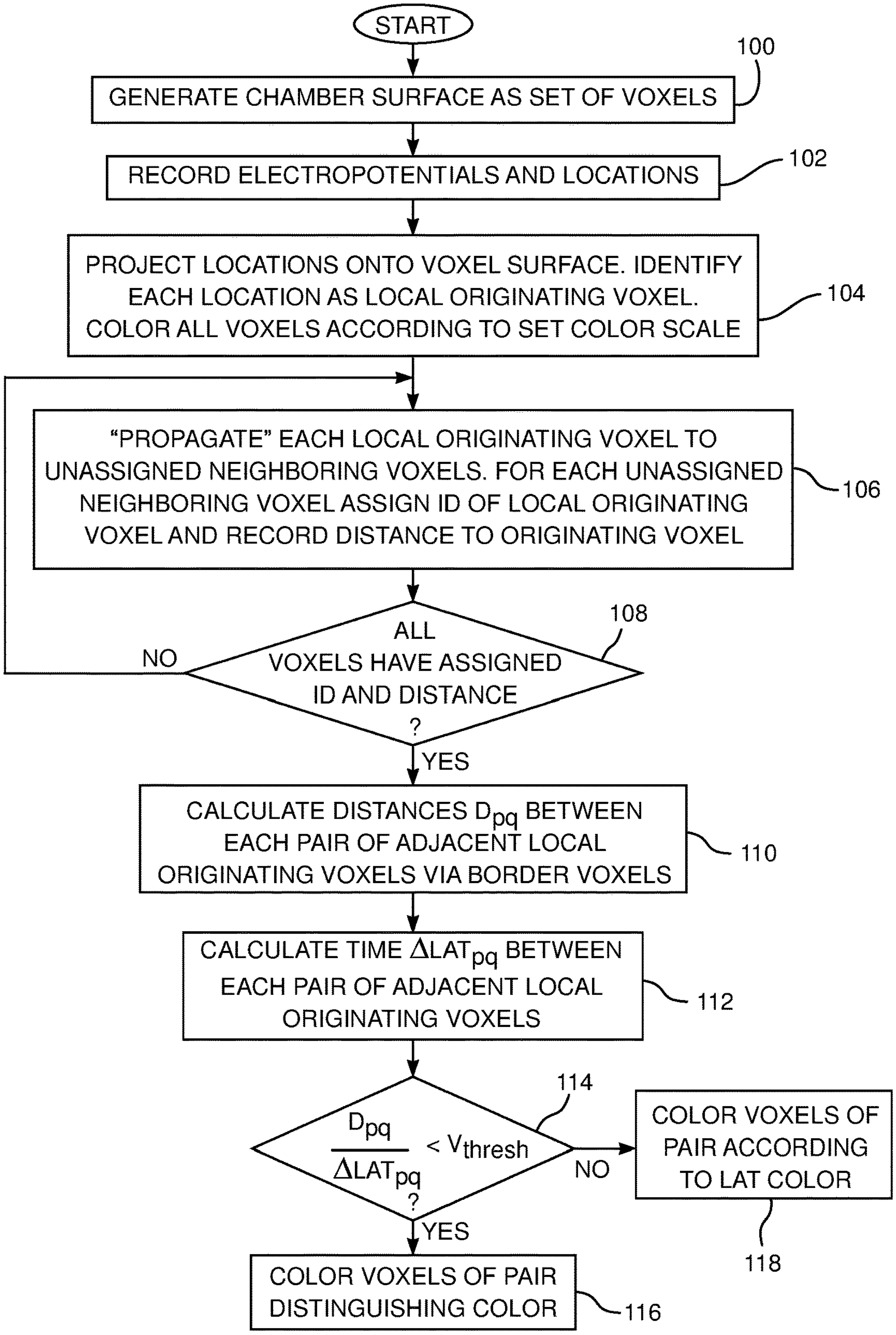
FIG. 3 is a flowchart of steps performed during operation of the apparatus, according to an embodiment of the present invention.
Figure 4A:
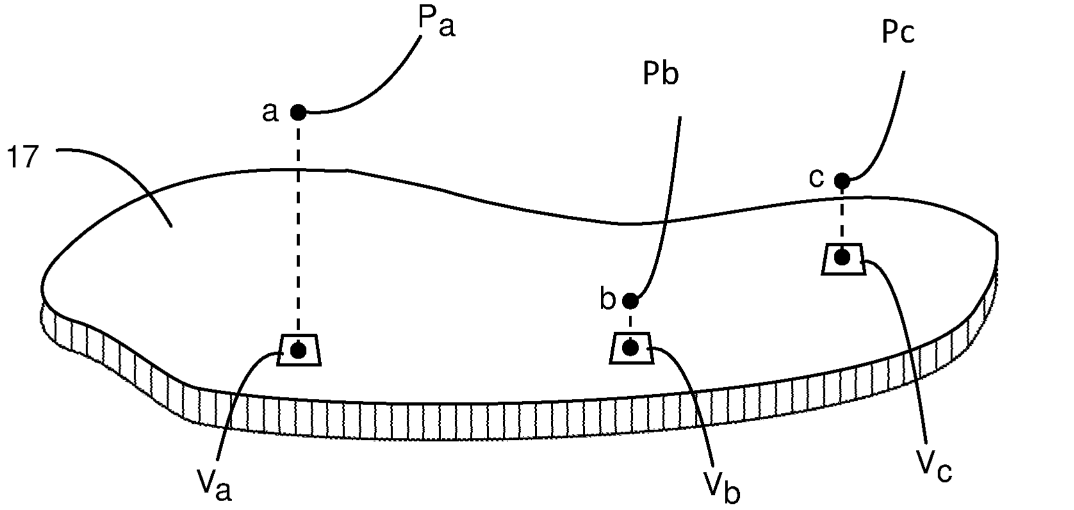
FIGS. 4A, 4B, and 5 illustrate some of the steps of the flowchart, according to an embodiment of the present invention.
Figure 4B:
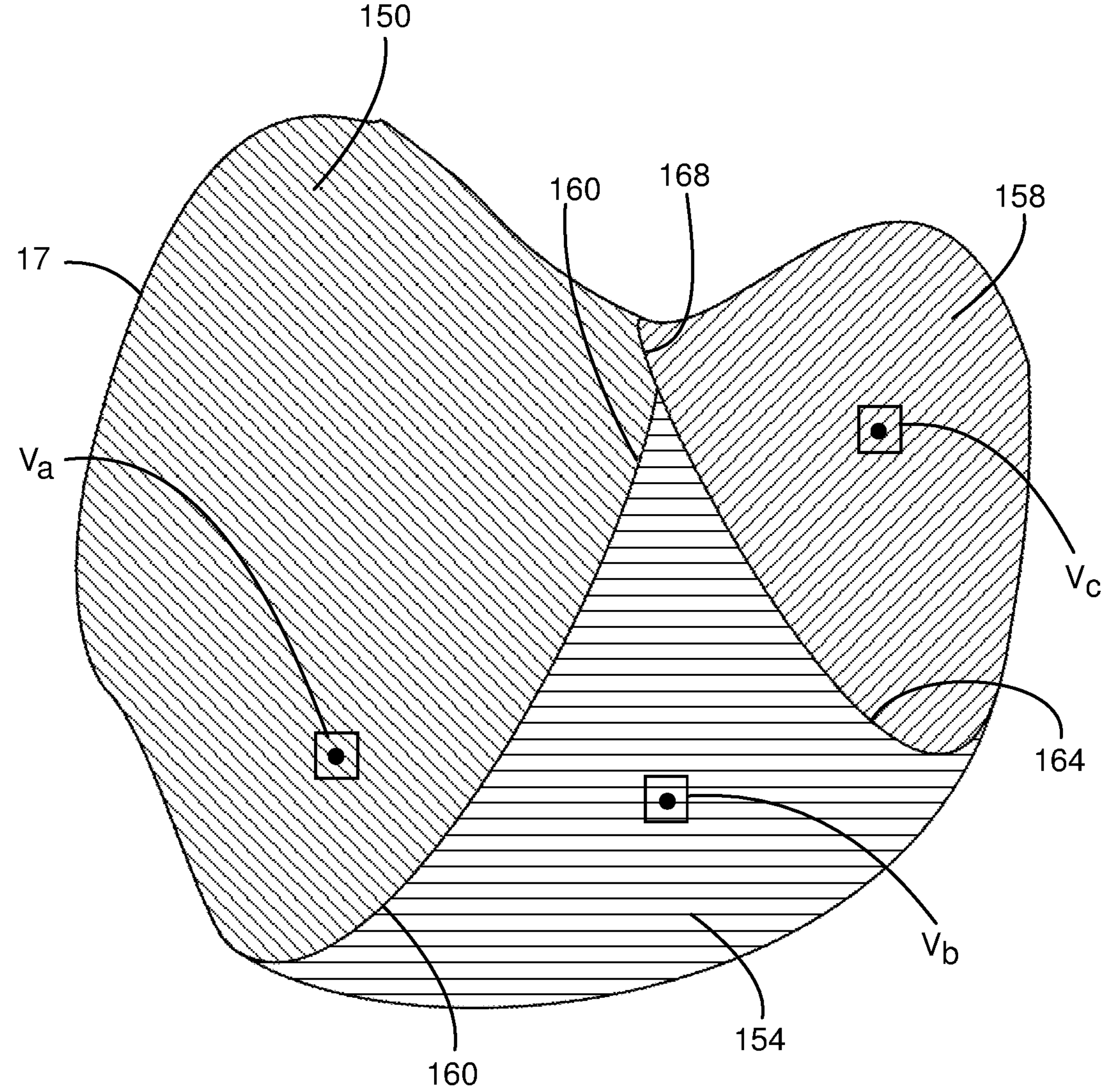
Figure 5:
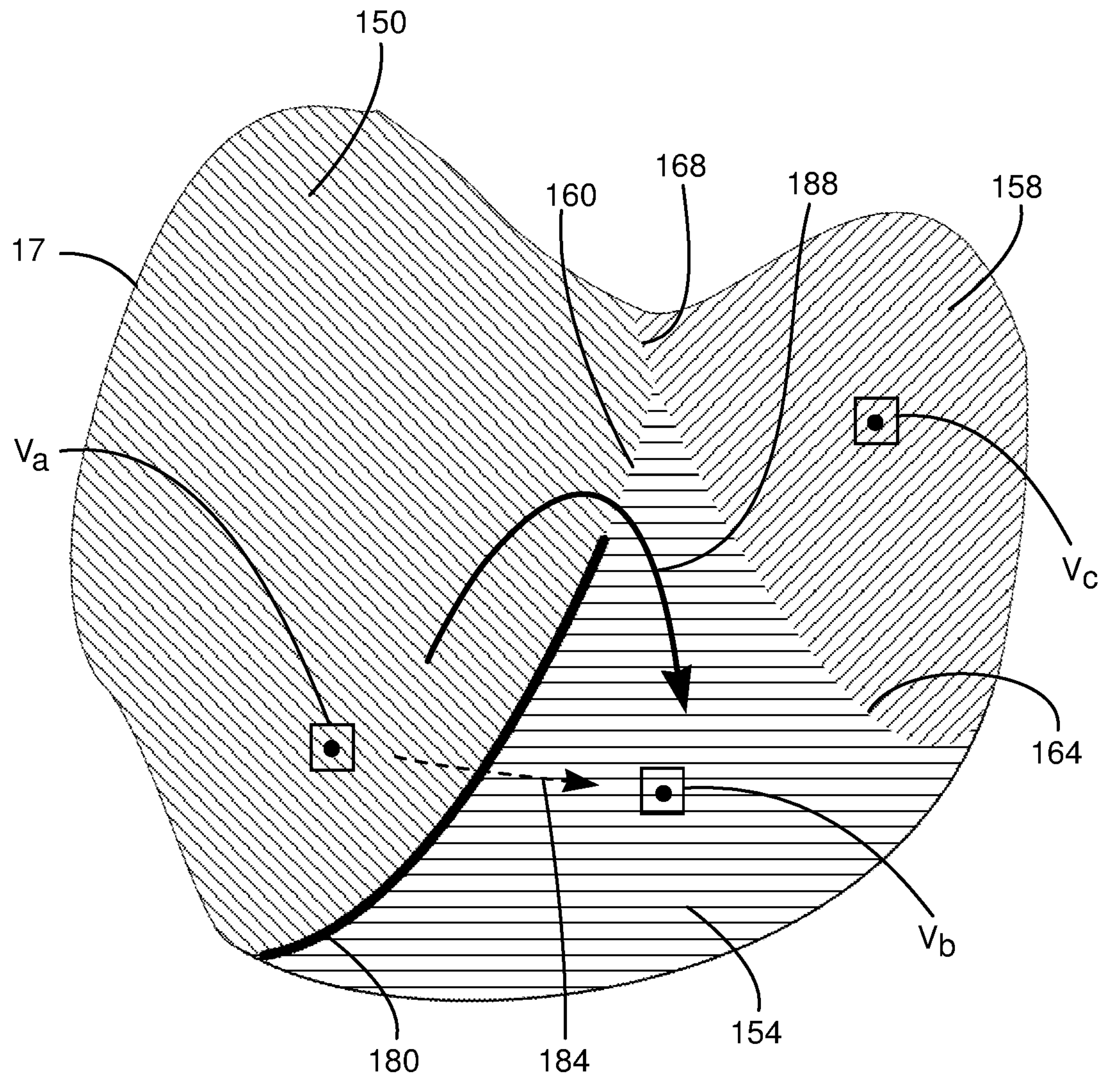

FIG. 3 is a flowchart of steps of an algorithm performed by processor 46 in conjunction with medical professional 14 during operation of apparatus 12, and FIGS. 4A, 4B, and 5 illustrate some of the steps, according to an embodiment of the present invention. The flowchart describes steps of mapping the 3D surface 17 of chamber 15, and also of acquiring signals from the surface 17. While in some embodiments these two functions are performed by separate probes, for simplicity, in the description below probe 20 is assumed to perform both these functions. Implementation of embodiments for the case of different probes being used for the different functions is also considered to be within the scope of the present invention.

In an initial step 100 a 3D map of surface 17 of chamber 15 of the heart 16 of patient 18 is produced. The production is typically performed by inserting distal end 22 into the chamber 15 and moving the distal end 22 within the chamber 15. As the distal end 22 is moved, tracking module 58 acquires successive data location signals from position sensor 24, and the module together with processor 46 analyze each of the signals to produce respective 3D locations for the distal end 22.

Processor 46 analyzes the set of 3D locations, which are effectively a point cloud, to produce a mesh enclosing the point cloud, and from the mesh the processor generates surface 17 of the chamber as a set of voxels. Methods for generating an enclosing mesh and a corresponding surface for a point cloud are well known in the art.

In a signal acquisition step 102, electrode 30 of distal end 22 is touched on different points of surface 17, and at each point the location P of the point being touched is derived from signals acquired from sensor 24.

At the same time, signals generated at the point being touched are acquired from electrode 30 by ECG module 56, which also records the signals. For any given point 'a' the signal acquired is a set of voltage time ordered pairs: $\{(V_t, t)\}_a$, where $V_t$ is the electropotential at a time t. In some embodiments $\{(V_t, t)\}_a$ may be presented to professional 14 as a voltage vs. time graph on display 62.

ECG module 56 and processor 46 analyze each of the recorded signals, $\{(V_t, t)\}$, to derive a respective local activation time (LAT) for each of the points touched by electrode 30. The analysis is represented by equation (1):

$$LAT_a = f[\{(V_t,t)\}_a] \quad (1)$$

where a is an identifier for the point on surface 17, and f represents the function applied to $\{(V_t, t)\}$ to derive the local activation time at point a, $LAT_a$.

As stated above, the value of $LAT_a$ is typically a time measured relative to a predetermined reference time signal, such as that provided by a reference probe inserted into the coronary sinus of heart 16.

Thus, for a given point a, step 102 finds the ordered pair (location, local activation time): ($P_a$, $LAT_a$).

Because of the beating of heart 16, the surface mapped in step 100 is not a stationary surface, so that the locations of points touched by electrode 30, and derived in step 102, typically may not coincide with the surface generated in step 100. A projection step 104 addresses this point.

In projection step 104, processor 46 projects each of the locations found in step 102 onto voxel surface 17 derived in step 100. FIG. 4A is a schematic illustration of the projection, and shows by way of example the locations $P_a$, $P_b$, $P_c$, of three points a, b, c, in proximity to 3D surface 17. The projections are to respective voxels $V_a$, $V_b$, $V_c$ of the surface. In step 104 the processor stores the set of voxels found by projecting all the points determined in step 102. The voxels derived from the projections are herein termed local originating voxels.

The local originating voxels are colored according to scale 64, using the respective LAT value of the locations that are projected. The LAT values of intermediate voxels on surface 17, i.e., voxels that are not local originating voxels, are typically determined by interpolation, and the intermediate voxels are also colored according to scale 64. In one exemplary embodiment the interpolation for an intermediate voxel finds an average of the LAT values of the nearest local originating voxels, weighted according to the distance to the local originating voxels.

In a propagation step 106 processor 46 defines a respective region in 3D surface 17, i.e., a respective set of voxels, around each local originating voxel. In order to define each region, the processor defines a common identifier $V_{id}$ for each of the voxels in the region, where id is a numerical identifier of the region and also of the region's local originating voxel. As is explained below, the processor also measures a distance D, over 3D surface 17, for each of the voxels in a region from its local originating voxel. Thus, each voxel in a given region has an ordered pair (voxel identifier, distance to local originating voxel), herein written as ($V_{id}$, D), associated with it. The ordered pair for each local originating voxel of a region is ($V_{id}$, 0).

After defining the ordered pairs for each of the local originating voxels: ($V_1$, 0), ($V_2$, 0), ($V_3$, 0), . . . the processor assigns the other voxels of surface 17 to have temporary ordered pairs enabling the processor to distinguish the non-local originating voxels from the local originating voxels. By way of example, in the following description all the non-local originating voxels are assigned ordered pairs (0, 0); i.e., the identifiers of non-local originating voxels are assigned the value 0.

However, other methods of distinguishing non-local originating voxels from the local originating voxels are assumed to be comprised within the scope of the present invention.

Once all the voxels of surface 17 have been assigned ordered pairs as described above, the processor proceeds to "propagate" the identifier of each of the local originating voxels. To implement the propagation, for a given local originating voxel with identifier $V_g$ the processor determines an immediately neighboring voxel and checks if the first term of the ordered pair, the identifier of the voxel, is 0.

If it is 0, the processor assigns the voxel the identifier $V_g$, and also calculates the distance D to the local originating voxel, which is assigned to the second term of the voxel's ordered pair.

If the identifier of the voxel is not 0, the processor performs the check on another immediately neighboring voxel, and continues until all immediately neighboring voxels have been checked The processor proceeds with further non-local originating voxels that neighbor the checked immediately neighboring voxels, in each case checking if a voxel identifier is 0. For each voxel having an identifier 0, the processor assigns the voxel the identifier $V_g$. The processor also calculates the distance D over 3D surface 17 to the local originating voxel, by adding the distance between the two voxels being compared to the distance of the voxel with the already existing identifier $V_g$. It will be understood that the distance assigned to any particular voxel is equal to the accumulated distances between all the intermediate neighboring voxels.

The process described above iterates, so that a contiguous region of voxels grows around the local originating voxel. Each of the voxels of the growing region has an identifier $V_g$ common with that of the local originating voxel, and a distance D, equal to the distance calculated over 3D surface 17, from the local originating voxel.

Processor 46 applies the process described above simultaneously to all local originating voxels, so that during the process implemented by step 106 there are a multiplicity of growing regions, each region originating with a local originating voxel. It will be understood that each region terminates growing when the processor finds no further neighboring voxels having an identifier 0, and when at least one of the neighboring voxels has an identifier different from that of the local originating voxel.

A condition 108 checks if all voxels of surface 17 have been assigned an identifier and a distance to a local originating voxel. If the condition returns negative, the processor continues with propagation step 106.

If the condition returns positive, control continues to a distance calculating step 110, described below. It will be understood that on completion of the process described above for step 106 surface 17 is divided into a set of contiguous regions which are touching, i.e., which have no gaps between the regions. Each region comprises a set of contiguous voxels having a common voxel identifier, corresponding to the identifier of the local originating voxel of the region. Each voxel of a given region is also associated, as described above, with a distance, measured over 3D surface 17, to the local originating voxel of the given region.

FIG. 4B schematically illustrates the conclusion of step 106, showing, by way of example, three regions 150, 154, 158, respectively associated with local originating voxels $V_a$, $V_b$, $V_c$, on surface 17. Each region is bordered by at least one other region, and in the example illustrated, each region is bordered by two regions. Thus, there is a border 160 between regions 150 and 154, a border 164 between regions 154 and 158, and a border 168 between regions 158 and 150.

In FIG. 4B region borders 160, 164, and 168 are for clarity shown as solid lines; however, it will be understood that in practice the borders of regions around local originating voxels are not visible on the representation of surface 17 presented on display 62. Furthermore, it will be understood that because the region borders generated in step 106 are not associated with LAT values of the border voxels, there is typically no relation between the interpolated colors (as found in step 104) of the border voxels, and the location of the border voxels.

A region border comprises a set of n voxels, where n is a positive integer, each border voxel having the same identifier as the identifier of the local originating voxel. In addition, each border voxel has at least one nearest neighboring voxel with an identifier different from that of the local originating voxel. Thus, if local originating voxel $V_a$ of region 150 has an identifier A, and if local originating voxel $V_b$ of region 154 has an identifier B, then each of the n border voxels in region 150 at border 160 has an identifier A, and each of these border voxels has a nearest neighbor with an identifier B. There is a corresponding set of voxels in region 154 at border 160, each of these voxels having an identifier B and a nearest neighbor with an identifier A.

When condition 108 returns positive, the processor records the locations of all n voxels of each border.

In distance calculating step 110, the processor analyzes the parameters associated with the border voxels in order to calculate distances, measured over 3D surface 17, between neighboring local originating voxels. In border 160 the n border voxels of region 150 have respective ordered pairs: (A, $D_{Va1}$), (A, $D_{Va2}$), (A, $D_{Va3}$), . . . , (A, $D_{Van}$), where $D_{Van}$ is the distance of the $n^{th}$ border voxel of border 160 to local originating voxel $V_a$. Each of the n border voxels of border 160 has at least one nearest neighbor voxel with an identifier B. There is thus a set of n border voxels in region 154 with respective ordered pairs (B, $D_{Vb1}$), (B, $D_{Vb2}$), (B, $D_{Vb3}$), . . . , (B, $D_{Vbn}$), where $D_{Vbn}$ is the distance of the $n^{th}$ border voxel of border 160 to local originating voxel $V_b$.

For border 160 processor 46 selects pairs of adjacent border voxels. For a given pair one voxel is in region 150, the other voxel is in region 154. Each pair has parameters (A, $D_{Vak}$), (B, $D_{Vbk}$) where k is an integer between 1 and n. The distance from local originating voxel $V_a$ to local originating voxel $V_b$, via the border pair of voxels with parameters (A, $D_{Vak}$), (B, $D_{Vbk}$), is given by:

$$D_{abk}=D_{vak}+D_{vbk} \quad (2)$$

Step 110 concludes when the processor has calculated all the distances between neighboring local originating voxels, via respective border voxel pairs, for all of the borders generated in step 106, using equation (2). For two generic neighboring regions p, q, the distances are referred to herein generically as $D_{pq}$.

In a timing step 112, the processor calculates the difference in local activation times between adjacent local originating voxels. In order to calculate the difference, the processor first estimates a median cycle length, CL, of heart 16, i.e., a median time period between successive heart chamber activations. The processor may estimate CL by any convenient means, such as analyzing times derived from the coronary sinus reference probe referred to above or analyzing times from a body surface electrode.

To account for the cyclic nature of the LAT values, the processor then calculates the difference in LATs between adjacent local originating voxels according to the following equation:

$$\Delta LAT_{pq}=\min(|LAT_p-LAT_q|,[CL-|LAT_p-LAT_q|]) \quad (3)$$

where $LAT_p$, $LAT_q$ are the LATs of respective local originating voxels of neighboring regions p,q, and $\Delta LAT_{pq}$ is the difference of the LATs.

In step 112 the processor calculates the values of $\Delta LAT_{pq}$ for all pairs of adjacent regions p,q on surface In a comparison step 114, for every border voxel pair, as determined in step 110, the processor calculates the ratio $$\frac{D_{pq}}{\Delta LAT_{pq}}.$$

It will be understood that this ratio corresponds to the velocity of the conduction wave as it transfers between the local originating voxels of regions p, q, via the border voxel pair that is being considered.

The processor then checks if the calculated velocity is below a preset threshold velocity, $V_{threshold}$, i.e., the processor checks if expression (4) is valid. A typical value for $V_{threshold}$ is approximately 0.1 mm/ms, while a typical range for $V_{threshold}$ is approximately 0.01 mm/ms—approximately 1 mm/ms.

$$\frac{D_{pq}}{\Delta LAT_{pq}} < V_{Threshold} \quad (4)$$

If the comparison of expression (4) returns positive, i.e., the calculated velocity is below the preset threshold velocity, then in a distinguishing color step 116 the processor colors the border voxel pair under consideration a distinguishing color, different from the colors of scale 64. For example, if brown is not in color scale 64, the processor may color the pair of border voxels, for which expression (4) is positive, brown.

FIG. 5 illustrates a case where the comparison of expression (4) returns positive. FIG. 5 is generally similar to FIG.

4B, but in contrast to FIG. 4B, borders 160, 164, 168 have not been illustrated with solid lines; however, the borders are still present.

In FIG. 5 a line 180 is assumed to comprise pairs of border voxels, in border 160, where expression (4) returns positive. Thus, from step 116, the pairs of voxels of line 180 are colored a distinguishing color, different from the colors of scale 64.

The presentation of a differently colored region, such as that for line 180, assists medical professional 14 in deciding a direction of travel of the conduction wave through the heart. The line effectively illustrates a blockage to a wave that may be travelling from region 150 to region 154. Thus, rather than a broken arrow 184 being a possible wave path, the conduction wave probably travels along a path similar to that of a solid arrow 188.

Returning to the flowchart of FIG. 3, if the comparison of expression (4) returns negative, i.e., the calculated velocity is equal to or above the preset threshold velocity, then in a standard color step 118 the processor colors the border voxel pair according to scale 64, i.e., by using their interpolated LAT values to select a corresponding color from the scale.

As used herein, the term "approximately" for any numerical values or ranges indicates a suitable dimensional tolerance that allows the part or collection of components to function for its intended purpose as described herein. More specifically, "approximately" may refer to the range of values ±10% of the recited value, e.g. "approximately 90%" may refer to the range of values from 81% to 99%.

It will be appreciated that the application of a distinguishing color in step 116 is but one method of indicating that a set of border voxels have velocities below a preset threshold, and other distinguishing methods, such as overlaying a broken line on the voxels, are assumed to be comprised with the scope of the present invention.

It will thus be appreciated that the embodiments described above are cited by way of example, and that the present invention is not limited to what has been particularly shown and described hereinabove. Rather, the scope of the present invention includes both combinations and sub combinations of the various features described hereinabove, as well as variations and modifications thereof which would occur to persons skilled in the art upon reading the foregoing description and which are not disclosed in the prior art.

The invention claimed is:

1. An apparatus for electropotential investigation of a 3-D surface, the apparatus comprising:

a catheter, configured to be inserted into a chamber of a heart and comprising one or more electrodes configured to contact myocardial tissue at multiple locations in the chamber and to sense electrical signals responsive to a conduction wave traveling through the tissue; and a processor, configured to:

receive the electrical signals from the catheter;

render on a display, a surface of the chamber as a set of voxels, the surface being displayed as a voxel surface of the chamber, derive a local activation time (LAT) for each location in the chamber contacted by the catheter from the sensed electrical signals, the LAT including a location and a value, project each location onto the voxel surface to establish corresponding local originating voxels on the display and color each local originating voxel according to a set scale based upon the LAT value of the projected locations, determine, iteratively, immediately neighboring intermediate voxels for each local originating voxel, each intermediate voxel having a determined distance from its corresponding local originating voxel, and color each intermediate voxel according to the set scale so as to divide the surface of the chamber on the display into contiguous regions of voxels around the local originating voxels respectively, each region being bordered by at least one other region and each region having a border comprising a plurality of sets of pairs of border voxels, determine distances between pairs of local originating voxels via respective border voxels for each border of each region, determine, for each border voxel pair, a difference in LAT between adjacent local originating voxels and a velocity of the conduction wave as it transfers between the local originating voxels via respective border voxel pairs, and color on the display, the border voxel pair under consideration a color different than the color of the set scale when the velocity is below a present threshold and a color according to the set scale when the velocity is equal to or above the preset threshold.

2. The apparatus according to claim 1 wherein the processor is configured to iteratively determine intermediate voxels using interpolation.

3. The apparatus according to claim 1, wherein the electrical signals comprise electrocardiograph (ECG) signals, and wherein the LATs are derived from the ECG signals.

4. The apparatus according to claim 3, wherein the processor is configured to incorporate into the set scale respective colors in a one-to-one correspondence with values of the LATS.

5. The apparatus according to claim 1, wherein the preset threshold is between 0.01 mm/ms and 1 mm/ms.

6. The apparatus according to claim 1, wherein the preset threshold is 0.1 mm/ms.

7. The apparatus according to claim 1, wherein the catheter comprises a position sensor configured to provide location signals indicative of the multiple locations to the processor.

8. The apparatus according to claim 7, wherein the position sensor comprises one or more coils which provide the location signals in response to magnetic fields traversing the coils.

9. A method for electropotential investigation of a 3-D surface, the method comprising:

inserting a catheter into a chamber of a heart, the catheter comprising one or more electrodes configured to contact myocardial tissue at multiple locations in the chamber and to sense electrical signals responsive to a conduction wave traveling through the tissue;

receiving the electrical signals from the catheter;

rendering on a display, a surface of the chamber as a set of voxels, the surface being displayed as a voxel surface of the chamber, deriving a local activation time (LAT) for each location in the chamber contacted by the catheter from the sensed electrical signals, the LAT including a location and a value, projecting each location onto the voxel surface to establish corresponding local originating voxels on the display and color each local originating voxel according to a set scale based upon the LAT value of the projected locations, determining, iteratively, immediately neighboring intermediate voxels for each local originating voxel, each intermediate voxel having a determined distance from its corresponding local originating voxel, and color each intermediate voxel according to the set scale so as to divide the surface of the chamber on the display into contiguous regions of voxels around the local originating voxels respectively, each region being bordered by at least one other region and each region having a border comprising a plurality of sets of pairs of border voxels, determining distances between pairs of local originating voxels via respective border voxels for each border of each region, determining, for each border voxel pair, a difference in LAT between adjacent local originating voxels and a velocity of the conduction wave as it transfers between the local originating voxels via respective border voxel pairs, and coloring, on the display, the border voxel pair under consideration a color different than the color of the set scale when the velocity is below a present threshold and a color according to the set scale when the velocity is equal to or above the preset threshold.

10. The method according to claim 9 further comprising iteratively determining intermediate voxels using interpolation.

11. The method according to claim 9, wherein the electrical signals comprise electrocardiograph (ECG) signals, and wherein the LATs are derived from the ECG signals.

12. The method according to claim 11, and comprising incorporating into the set scale respective colors in a one-to-one correspondence with values of the LATs.

13. The method according to claim 9, wherein the preset threshold is between 0.01 mm/ms and 1 mm/ms.

14. The method according to claim 9, wherein the preset threshold is 0.1 mm/ms.

15. The method according to claim 9, wherein the catheter comprises a position sensor configured to provide location signals indicative of the multiple locations.

16. The method according to claim 15, wherein the position sensor comprises one or more coils which provide the location signals in response to magnetic fields traversing the coils.

* * * * *